United States Patent [19]

Spilker et al.

[11] Patent Number: 5,686,724
[45] Date of Patent: Nov. 11, 1997

[54] METHOD FOR DETERMINING OIL CONTENT OF AN UNDERGROUND FORMATION USING WET CUTTINGS

[75] Inventors: Kerry Kennedy Spilker; Patrick Lee DeLaune, both of Houston; Howard Lee McKinzie, Sugar Land, all of Tex.

[73] Assignee: Texaco Inc., White Plains, N.Y.

[21] Appl. No.: 637,982

[22] Filed: Apr. 26, 1996

Related U.S. Application Data

[60] Provisional application No. 60/012,846, Mar. 5, 1996.
[51] Int. Cl.$^6$ .............................. G01V 9/04; G01N 21/64
[52] U.S. Cl. ..................... 250/255; 250/301; 250/461.1
[58] Field of Search ............................... 250/255, 301, 250/461.1

[56] References Cited

U.S. PATENT DOCUMENTS

| | | | |
|---|---|---|---|
| 2,367,664 | 1/1945 | Campbell et al. | 250/255 |
| 2,431,487 | 11/1947 | Larsen | 250/301 |
| 4,977,319 | 12/1990 | Supernaw | 250/225 |

*Primary Examiner*—Carolyn E. Fields
*Attorney, Agent, or Firm*—Henry H. Gibson; William J. Beard

[57] ABSTRACT

Methods are disclosed for evaluating wet cutting from a well borehole to determine the hydrocarbon content of the earth formations penetrated by the well borehole. The wet cuttings to be measured are mixed with a polar hydrocarbon solvent which has both hydrophilic and hydrophilic properties. The solution of the solvent and cutting is filtered and then its emission (fluorescence) spectrum is measured by irradiating it with ultraviolet radiation excitation at wavelengths at which most petroleum compounds fluoresce. The hydrocarbon content of the sample wet cuttings is then determined by comparing its fluorescence emission to the emission fluorescence of known samples.

9 Claims, 6 Drawing Sheets

(4 of 6 Drawing(s) in Color)

METHOD FOR DETERMINING OIL CONTENT OF AN UNDERGROUND FORMATION USING WET CUTTINGS

CROSS REFERENCE

This application is a continuation-in-part of Provisional application Ser. No. 60/012,846, filed Mar. 5, 1996.

FIELD OF THE INVENTION

This invention is related to methods for determining the presence of hydrocarbons in an underground formation. More particularly, this invention concerns a new method which makes it possible to use wet cuttings in quantitative fluorescence measurements. Benefits of this method are significant reduction in cycle time and improved accuracy. According to the current state of the art, samples to be evaluated must be dried before being solvated in order to obtain accurate fluorescence analysis.

BACKGROUND OF THE INVENTION

Fluorescence has been used for decades as a logging technique for detecting oil in drill cuttings. For much of that time the method used to determine the presence of oil in drill cuttings was a crude method in which an operator shined a broad spectrum ultraviolet light source on the cuttings in order to see fluorescence which would indicate the presence of oil. This visual method is highly subjective and inconsistent.

Ultra-violet fluorescence spectroscopy is used for the measurement of petroleum hydrocarbons in drill cuttings, cores, and soil samples by fluorescence examination of solvent extracts of these solids.

Molecular fluorescence is discussed in general in *Principles of Instrumental Analysis*, by Skoog, Douglas, Sanders College Publishing, Philadelphia (3rd ed. 1985), pp 225-240. The discussion in this reference indicates that the greatest fluorescence behavior occurs with compounds containing aromatic functional groups. The authors also disclose several analytical profiles of hydrocarbons wherein fluorescence intensity is plotted over multiple excitation and emission wavelengths.

Fluorescence spectrophotometry is used for oil and gas prospecting via remote sensing or near surface sampling methods. In U.S.G.S. Open-File Report 84-385, 34 pp (1984), in an article by M. E. Henry and T. S. Donovan entitled "*Luminescense Properties and Chemical Geochemical Prospecting*", there is a discussion of the technology for this use.

The use of fluorescence techniques for geochemical prospecting is discussed in an article by C. F. Hebert entitled, "*Geochemical Prospecting for Oil and Gas Using Hydrocarbon Fluorescence Techniques*", 3RD Southern Methodist Univ. Symp.—Unconventional Methods in Exploration for Petroleum and Natural Gas, Processing, (1984), pp. 40-58.

The emission fluorescence of crude oil samples has been studied and recorded over various wavelengths, including ultraviolet wavelengths below 400 nm. There have been "fingerprint" studies, for example, at Bartlesville Energy Technology Center, where the emission fluorescence of various types of crude oils has been recorded at different excitation wavelengths. Research of this type at the Department of Energy was related to earlier work by the Bureau of Mines, the object of which was to identify crude oil by emission fluorescence for the purpose of pollution control. See Chisholm, B. R., Eldering, H. G., Giering, L. P., and Horning, A. W., "*Total Luminescence Contour Spectra of Six Topped Crude Oils*", BETC/RI-76/15, a paper prepared for ERDA for the Bartlesville Energy Research Center in Bartlesville, Okla., November 1976; and Brownrigg, J. T., and Hornig, A. W., "*Low Temperature Total Luminescence Contour Spectra of Six Topped Crude Oils and Their Vacuum Distillate and Residuum Fractions*", BETC/RI-78/13, a paper prepared for DOE for the Bartlesville Energy Technology Center, Bartlesville, Okla., July 1978.

In U.S. Pat. No. 4,977,319, incorporated herein by reference in its entirety, there is disclosed a method of determining the presence and concentration of hydrocarbons in a formation. The method involves the steps of solvating a sample from the formation in a known volume of solvent and measuring the emission fluorescence of the excited sample below about 400 nm and comparing the emission fluorescence to previous correlations drawn between known hydrocarbon contents of samples and the related emission fluorescence.

U.S. Pat. No. 4,990,773, incorporated by reference herein in its entirety, concerns a method of determining the producibility of any hydrocarbons present in a formation.

At present, in the art of evaluating hydrocarbons from underground formations it is accepted as necessary, to obtain accurate fluorescence data, to first dry drill cuttings before solvating in state of the art aliphatic solvents such as hexane, heptane, or pentane. It is known that emission fluorescence readings will vary with the degree of sample dryness. Water on the cuttings surface forms an impenetrable barrier to the aliphatic solvents and the amount of extracted crude oil is significantly reduced. Currently, samples must be air dried for evaluation. Drying time is dependent on the samples, environment, and equipment available to air dry samples without driving off hydrocarbons. Different formations require different drying times. Formation samples such as shale and sandstone dry in as little as 30 minutes. Clay cuttings require more time. Hot dry field conditions accelerate the drying process and damp humid conditions delay sample drying. Spin dryers and fans reduce the required drying time by removing excess water and increasing air flow, however, using these two devices, the minimum drying time is still about 15 minutes.

An additional disadvantage of having to dry cuttings is that the emission fluorescence after drying will vary according to the environment and volatility of the hydrocarbons present. Laboratory studies show a 50% decline in the emission fluorescence of a condensate over a 24 hour period due to the evaporation of volatile hydrocarbons. This phenomena has been particularly observed in the field where overnight drying is common.

Although the quantitative fluorescence method has provided a more accurate method of evaluating samples of underground formation than was previously available in the art, there is a need in the art for a method of extracting oil from wet drill cuttings to minimize volatilization of light prior to analysis and to improve the process and safety. It would significantly reduce sample processing problems and allow a technician to keep up with the drilling rate if it were possible to evaluate wet cuttings without a loss of accuracy. It would constitute a significant advance in the field if the resulting readings were found to exhibit fewer variations and to be more accurate.

SUMMARY OF THE INVENTION

In accordance with the foregoing, the instant invention comprises an improvement in a method for evaluating a sample of an underground formation to determine the hydrocarbon content of the formation by:

solvating a known volume of the dried sample, quantitatively measuring with a fluorometer the emission fluorescence of the solvated sample, and determining the hydrocarbon content of any hydrocarbon present in the sample by comparing the emission fluorescence of said solvated sample to emission fluorescence of hydrocarbon samples from known sources, the composition of which has already been determined, wherein said improvement allows for the determination of hydrocarbon concentration using wet cuttings samples, in contrast to washed and dried cuttings and comprises:

adding said sample to a polar solvent having dual functionality to solvate water and hydrocarbons, mixing said solvent and said sample, filtering said solvent/wet sample solution and quantitatively measuring with a fluorometer the emission fluorescence of the solvated sample below about 400 nm at an excitation wavelength at which most petroleum compounds fluoresce, and determining the hydrocarbon content of any hydrocarbon present in the sample by comparing the emission fluorescence of said solvated sample to the emission fluorescence of hydrocarbon samples from known sources, the composition of which has already been determined, wherein correlations are drawn between emission fluorescence of hydrocarbon samples from known sources and the emission fluorescence of the solvated sample.

BRIEF DESCRIPTION OF THE DRAWINGS

The file of this patent contains at least one drawing executed in color. Copies of this patent with color drawing(s) will provided by the Patent and Trademark Office upon request and payment of the necessary fee.

DETAILED DESCRIPTION OF THE INVENTION

Fluorescence is a phenomena wherein certain compounds, containing molecular arrangements generally referred to as chromophores, emit fluorescent radiation when excited by incoming light of certain wavelengths. The chromophores contained in compounds such as the asphaltenic, aromatic and resin fractions of crude, fluoresce in the ultraviolet and visible portion of the electromagnetic spectrum when bombarded with ultraviolet radiation of the proper excitation wavelength.

Single point (fixed excitation/emission wavelength) fluorescence measurements are used to determine the approximate quantity of oil in formation samples(QFT™). QFT™ is a tradename for Quantitative Fluorescence Technique™, a method for detecting oil in formations which was developed and patented by Texaco Inc., and is available for licensing. QFT™ can be accomplished with a relatively small, portable fluorometer.

By using a scale of fluorescence intensity and instrumentally measuring the fluorescence of a formation sample from cores or drill cuttings, a number proportional to the hydrocarbon content of the sample can be derived, as discussed in U.S. Pat. No. 4,977,319, supra.

The primary (most intense) peak for crude oils generally occurs in the spectral region between 300 nm and 360 nm. The position of the maximum fluorescence peak is dependent on the predominant fluorescing species(aromatics) found in the crude oil mixture.

The two to four-ring aromatics and their derivatives have considerable overlap in the 320 nm to 380 nm spectral range. Most of the heavier poly-aromatics consisting of five to six rings emit fluorescence from 400 nm and extend into the visible (410 nm to 800 nm.)

Total scanning (multiple excitation/emission wavelengths) fluorescence (TSF) measurements are used to further characterize oils/oil extracts and determine similarities of oils from different sources. TSF requires a relatively large, computer controlled instrument permanently installed in a laboratory environment.

In total scanning fluorescence or 3-D fluorescence, a sample is excited over a range of discrete wavelengths and the emitted radiation is recorded at various wavelengths. Total scanning fluorescence has indicated that the optimum excitation and emission wavelengths for most crude oils fall below 400 nanometers. This is a region undetectable by the human eye. The optimum excitation wavelength for most crude oils is in the region of about 250 to 310 nanometers. The predominant portion of emitted radiation falls in the non-visible ultraviolet region of about 300 to about 400 nanometers.

The method of the present invention would be most useful at the well site. Analysis can be obtained faster, with less time involved in analyzing, less error due to minimal volatilization of light ends, as well as minimal sample handling. The solvent is safer (higher flash point) and gives fewer false positives (e.g. asphaltic drilling and fluid additives).

At present hydrocarbon content is determined by first solvating a known volume of washed and air dried sample from the formation in a known volume of a solvent which will solvate hydrocarbons. The solvated sample is excited by a fluorometer at a fixed, relatively narrow, excitation wavelength. F1 intensity is measured at a similarly fixed, relatively narrow wavelength at which most petroleum compounds fluoresce. This value is proportional to the hydrocarbon content of the sample. The emission fluorescence of the solvated sample is then compared with samples having known concentrations of various hydrocarbons. Correlations can be drawn between the emission fluorescence of known samples having previously identified oil concentrations and the fluorescence of the samples in said solvent.

A wide variety of solvents capable of solvating hydrocarbons are currently used in the art to extract oils from dried formation samples. Preferred solvents are low molecular weight aliphatic hydrocarbons having four or more carbon atoms such as pentane, hexane, heptane and higher. Chlorinated hydrocarbons such as methylene chloride, chloroform, carbon tetrachloride, trichloroethane and others are also effective. However, strong solvents may lessen the accuracy of the method due to their ability to dissolve sample constituents other than hydrocarbons. Aromatic solvents are generally not preferred because of their inherent fluorescence.

It has now been discovered that certain solvents can be effectively used to solvate samples such as wet drill cuttings without the need for drying that is necessary with methods currently available in the art; and the resulting solvated wet cuttings will provide reliable fluorescence data. Generally, one set of suitable solvents are oxygenated hydrocarbons which exhibit hydrophilic and hydrophobic properties. The solvents must be capable of breaking through the water layer, solvating the commercially valuable components of the hydrocarbon, and not fluorescing significantly in the region of investigation. This would include a number of alcohols, acetates, and ketones. Examples include, but are not limited to, methanol, ethanol, ethyl acetate, 1-propanol, 2-propanol (isopropanol), 2-methyl-2-propanol, and allyl alcohol. Preferred solvents include methanol, ethanol, 2-propanol, and methyl-2-propanol, and combinations thereof.

In particular, 2-propanol, or isopropyl alcohol, is capable of breaking through the water barrier while, at the same time, solvating the aromatic portion without extracting the asphaltenes. The present invention demonstrates that polar solvents exhibiting dual functionalities can be used to effectively extract the desired hydrocarbons for emission fluorescence measurements in the presence of water.

The advantages of using a polar solvent with the hydrophobic and hydrophilic functionalities, such as 2-propanol (isopropyl alcohol- IPA), for QFT™ are:

1) The method provides the capability of extracting oil from wet drill cuttings, cores, and sidewall cores. It also significantly reduces sample processing problems and makes it possible for a technician to keep up with the drilling rate, providing immediate results, which is generally not possible with currently available methods using the normal alkanes, largely due to the time required for washing and air drying the samples. The reduction in cycle time improves the economics by reducing man hours spent on the sample analysis. The following figures show the magnitude of savings which could reasonably be expected:

|  | Dry Method | Wet Method |
| --- | --- | --- |
| Manpower, hrs. | 208 | 83 |
| Estimated Cost | $24,128.00 | $9,628.00 |
| Solvent Cost | $233.00 | $112.00 |

2) The method provides enhanced hydrocarbon detection due to the fact that the samples are analyzed before the volatile hydrocarbons are lost through the drying step. Field tests show up to a 50% or greater drop in QFT™ intensities over a 3 day period in drill cuttings containing condensates.

3) In the present invention a short chain alcohol having dual functionalities, such as isopropyl alcohol(2-propanol), more selectively extracts the components of commercial interest, providing a better indication of producibility in contrast to the commonly used heptane which is not useable in the presence of water and which also extracts portions of the tar, asphaltic and other nonproducible components.

4) The method of this invention provides a safer solvent system with a higher flash point, higher ignition temperature, lower heat of combustion, boiling point, and vapor density than heptane or hexane.

5) The method of this invention allows for as much as a 46% reduction in chemical costs compared to other solvents, as noted in the comparison above.

The following example(s) will further illustrate the method of solvating wet samples or cuttings. These examples are given by way of illustration and not as limitations on the scope of the invention. Thus, it should be understood that the steps of the invention method may be varied to achieve similar results.

EXAMPLE I (UV Fluorescence Ratios for Whole Oils)

Figure 1:
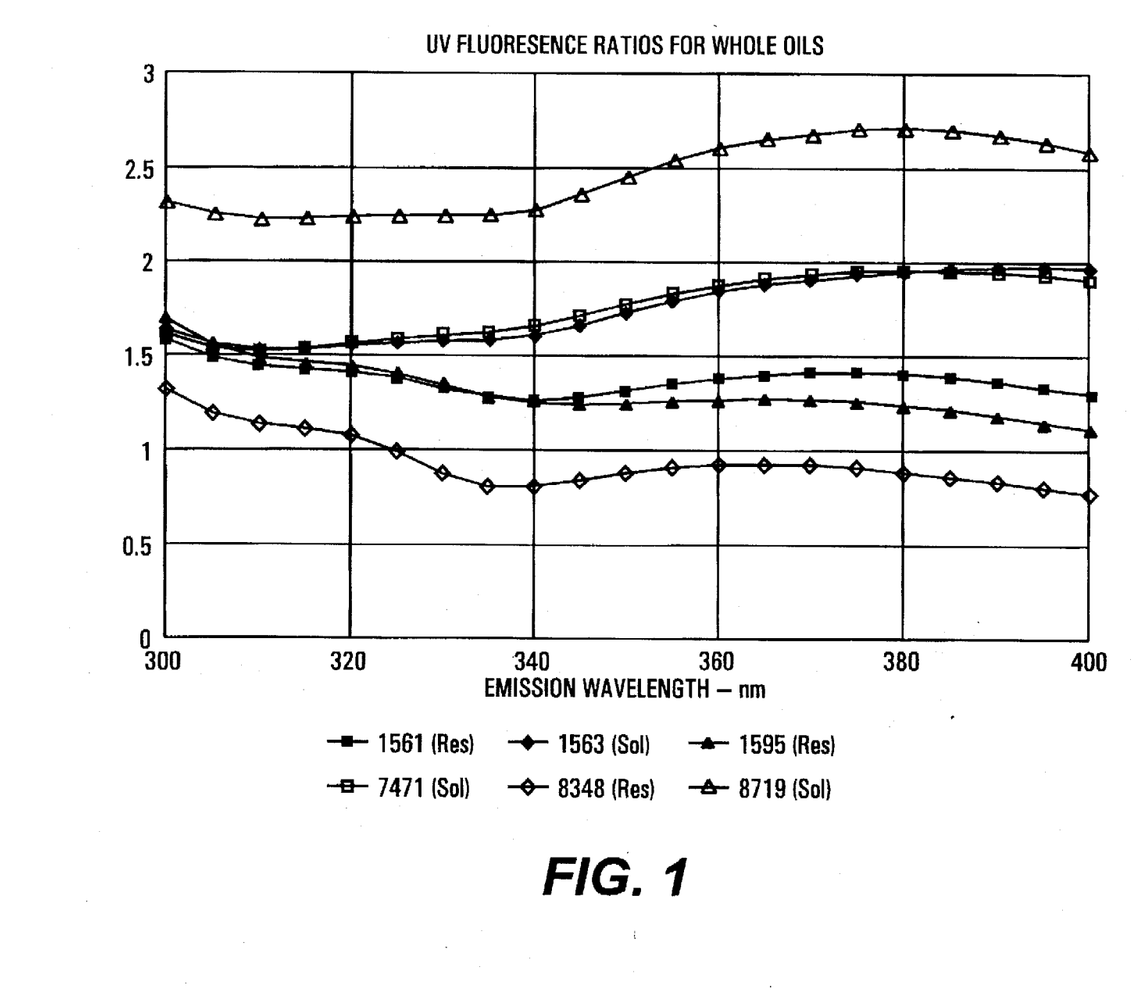
FIG. 1 is a graph showing the Intensity Ratio (the fluorescence intensity of an oil in isopropyl alcohol divided by the fluorescence intensity of the oil in heptane) as a function of wavelength. The fluorescence intensity per unit concentration in isopropyl alcohol is greater than the fluorescence intensity per unit concentration in heptane for all oils (has a value greater than 1.0) at 320 nm.
Figure 2:
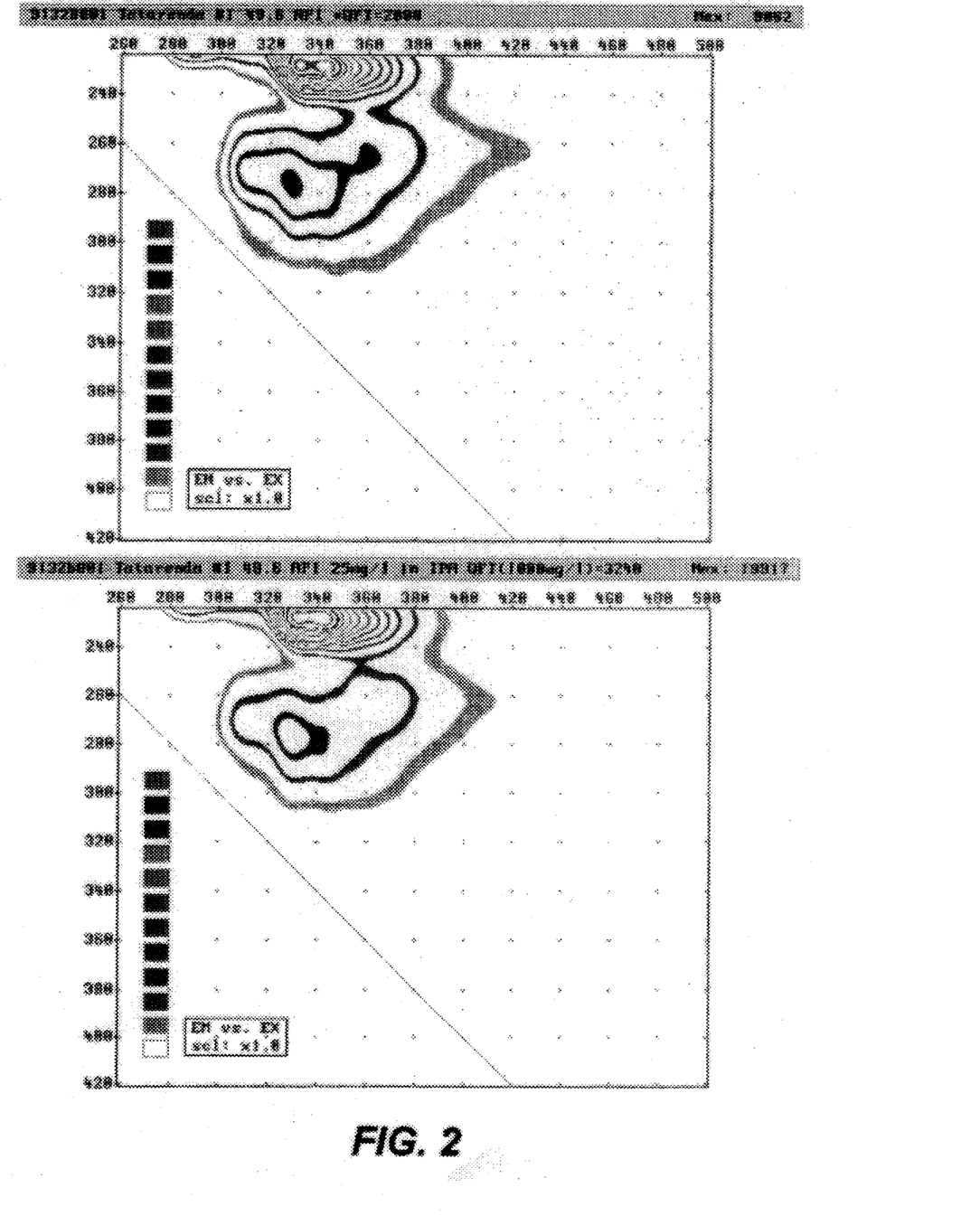
FIG. 2 is a total scanning fluorescence contour spectra of a 50 API gravity crude oil (condensate) dissolved in heptane and IPA.
Figure 3:
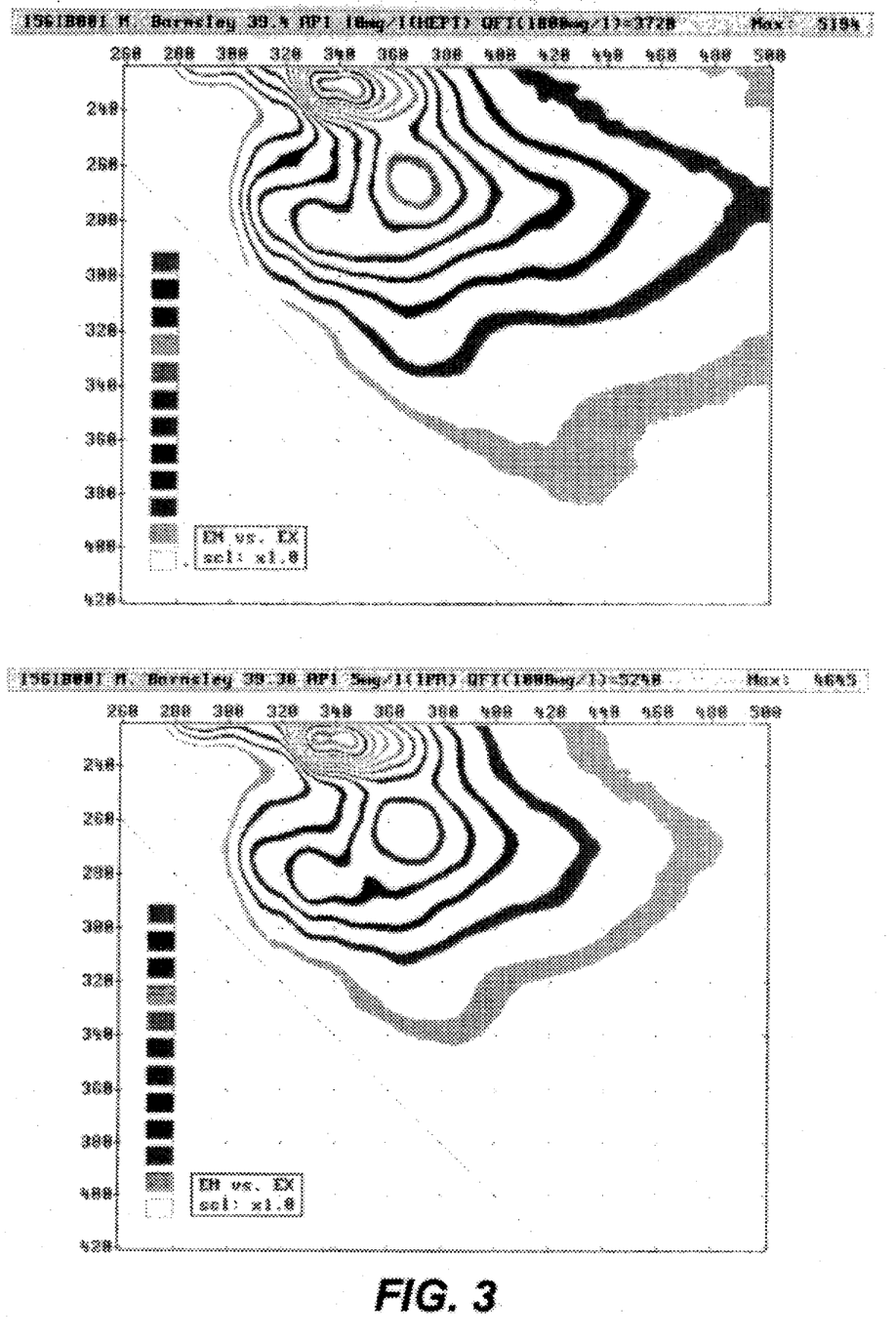
FIG. 3 is a total scanning fluorescence contour spectra of a 39 API gravity crude oil (light oil) dissolved in heptane and in IPA.
Figure 4:
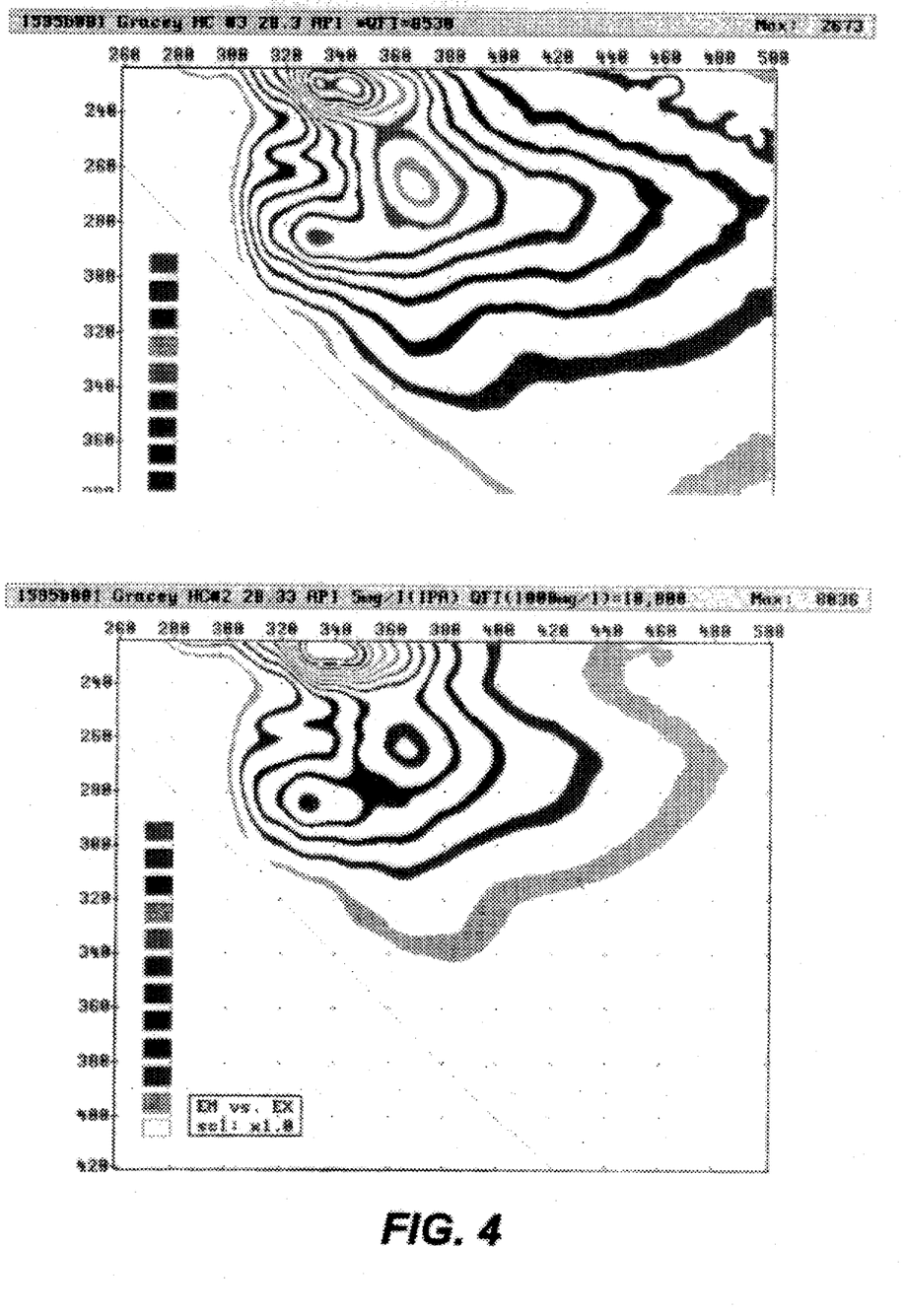
FIG. 4 is a total scanning fluorescence contour spectra of a 28 API gravity crude oil (medium oil), dissolved in heptane and IPA.
Figure 5:
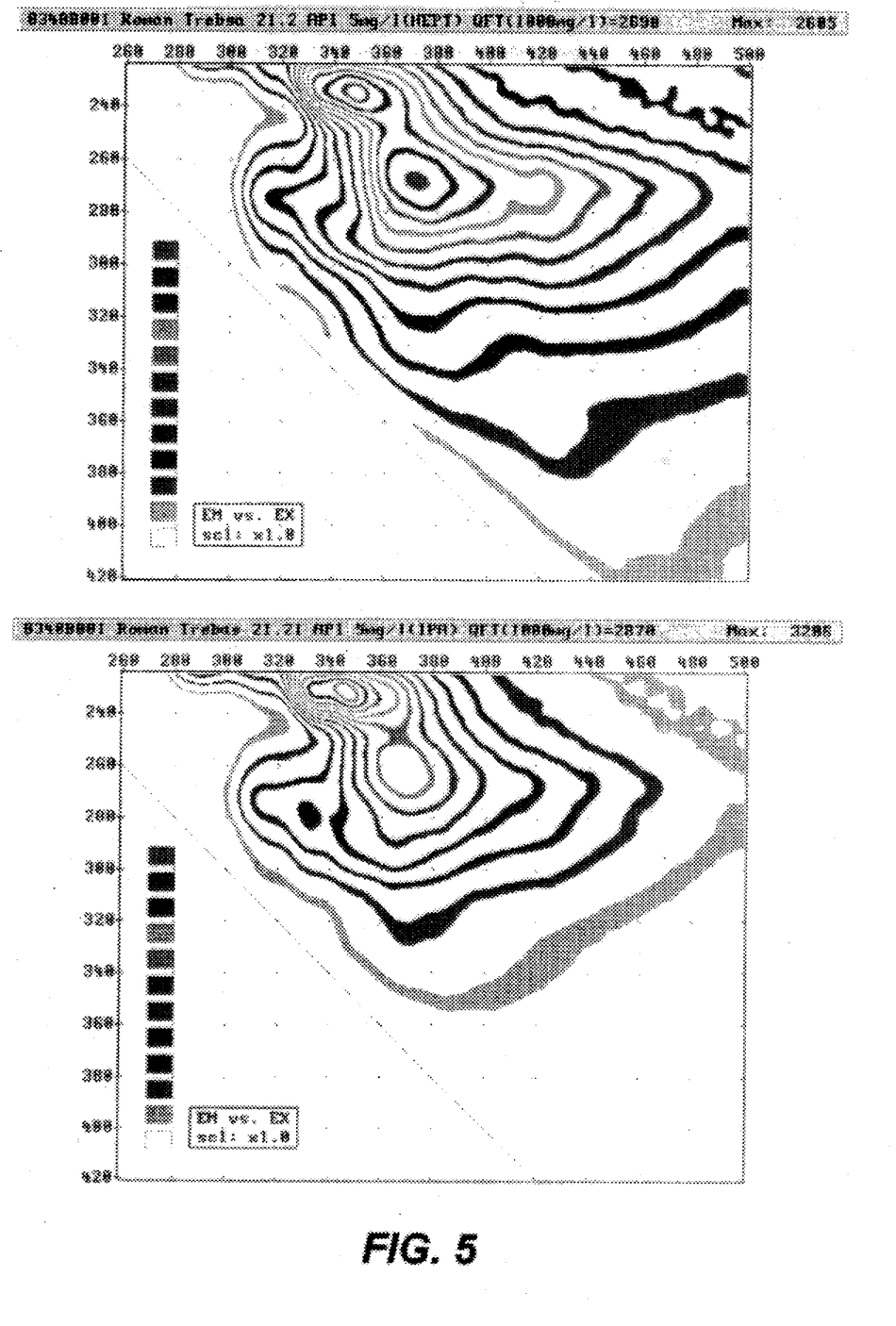
FIG. 5 is a total scanning fluorescence contour spectra of a 21 API gravity crude oil (heavy oil) dissolved in heptane and in IPA.

Several whole oils, varying in API gravity, were dissolved in heptane to make up 100 mg/l stock solutions. The same oils were used to prepare 100 mg/l stock solutions in IPA. The dissolved sample was visually inspected for solubility. All were soluble in heptane. Some were totally soluble in IPA, marked "sol", and others were partially soluble and left a residue and were labeled "res". All the solutions were diluted to less than 0.05 absorbance at 240 nm and analyzed using total scanning fluorescence. The fluorescence emission data from 300 nm to 400 nm at the 254 nm mercury excitation was collected using total scanning fluorescence (TSF) for each oil in each solvent. FIG. 1 is the Intensity Ratio (the fluorescence intensity of the oil in IPA divided by the fluorescence intensity of the oil in heptane) as a function of wavelength, nm for each oil. One can observe from FIG. 1 that at the QFT™ excitation and emission wavelength (254 nm/320 nm) the fluorescence intensity per unit concentration in IPA is greater (has a value greater than 1.0) than the fluorescence intensity per unit concentration in heptane for all oils evaluated.

EXAMPLE II

A series of cuttings were taken from different depths in a formation known to contain hydrocarbons. Equal amounts of each sample were used for three tests for samples from each depth. In the first test 0.5 gm. of the sample cuttings were washed and dried according to procedures presently known in the art and the air dried sample was solvated in 5 ml. of heptane. In the second test 0.5 gm. of the cuttings were washed, air dried, and solvated in 5 ml. isopropanol. Finally, 0.5 gm. of the cuttings were solvated in 5 ml. isopropanol without being washed and air dried.

Figure 6:
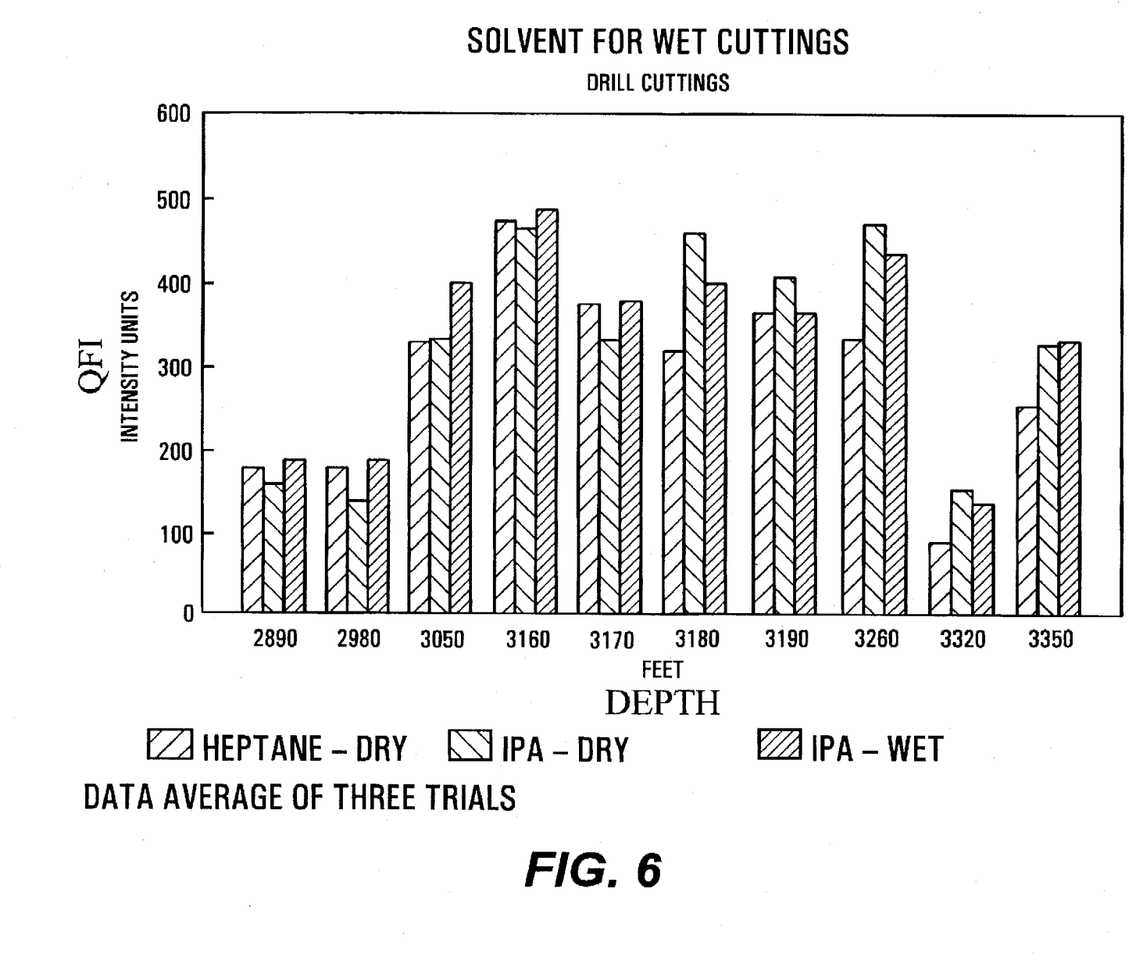
FIG. 6 is a bar graph comparing the accuracy of the results from the use of dry cuttings solvated in heptane and in isopropyl alcohol with wet cuttings solvated in isopropyl alcohol.

All solvated samples were excited by a fluorometer at a fixed, relatively narrow excitation wavelength and the emission results are represented in the bar graph in FIG. 6 and show that the QFT™ results are comparable when using heptane or IPA to extract drill cuttings.

The fluorometer used to determine wavelength emissions consisted basically of an ultraviolet light source, and excitation radiation filter between the light source and the sample, a photomultiplier tube which reads the intensity of radiation emitted by the sample at right angles to excitation radiation, and an emission filter placed between the sample and the photomultiplier tube. A reference light path between the light source and the photomultiplier was also provided so the difference between emitted radiation and exciting radiation can be easily determined. One suitable fluorometer which fits this description is a mud logging fluorometer commercially available from Turner Designs, 845 W. Maude Ave., Sunnyvale, Calif. 94086, under the name 10-AU-015.

The light source employed was a far ultraviolet source U tube having a Turner Model No. 110-851, GE No. G4T4/1 or equivalent. 95% of the radiation from this light source is a 254 nm, with some output at 297, 313, 405, 436, and 546 nm.

The excitation radiation filter employed was a Turner No. 7-54 filter which has a bell-shaped radiation transmission curve. This filter transmits about 80% of the radiation which strikes it from about 290 to about 360 nm, and 40% or more of incident radiation from about 250 nm to about 390 nm. Only 10% of incident radiation is transmitted at 236 and 400 nm. The end result of this combination of light source and excitation radiation filter is that 99% of the excitation radiation used in the examples was at 254 nm.

The emission filter employed was a 320 nm narrow band filter. The transmission curve of this emission filter allows 25% transmittance of incident radiation at 320 nm, dropping steeply to 20% transmittance at 313 nm and 327 nm. Transmittance is only 4% at 310 nm and 330 nm.

EXAMPLE III (QFT™ Fluorescence Ratios for Whole Oils)

This example compares oils of different API gravities dissolved in heptane versus IPA.

The purpose of this example was to illustrate that for the QFT™ measurement using the 10-AU-015 Mud Logging Fluorometer the same holds true, that although not all the oils are completely soluble in 2-propanol(IPA), the sensitivity is comparable to the heptane solvent or better.

| ID Number | API Gravity | Heptane (1000 mg/l) | IPA (1000 MG/L) | QFT™ Intensity Ratio |
|---|---|---|---|---|
| 1563 B001 | 60 | 1790 | 2520 | 1.41 |
| 9132 B001 | 50 | 2000 | 3240 | 1.62 |
| 8719 B001 | 45 | 4640 | 5080 | 1.09 |
| 1561 B001 | 39 | 3720 | 5240 | 1.41 |
| 7471 B001 | 33 | 9790 | 11200 | 1.14 |
| 1595 B001 | 28 | 6530 | 10800 | 1.65 |
| 8348 B001 | 21 | 2690 | 2870 | 1.07 |

The QFT™ fluorescence intensity per unit concentration in IPA is greater (has a value greater than 1.0) than the fluorescence intensity per unit concentration in heptane for all oils evaluated.

ADDITIONAL CONSIDERATIONS

The invention method is by no means limited to the combination of filters and light source employed. Other fluorometer and light sources, including lasers and filters, may be employed with the invention method with equal success. What the invention requires is that the solvated samples be radiated at an excitation wavelength at which most petroleum compounds fluoresce, generally below about 400 nm, preferably within the region of about 250 nm to about 400 nm. Although these examples were run with an excitation radiation of 254 nm and emission radiation measured at 320 nm, it may be desirable to change the wavelengths employed to better eliminate the effect of fluorescence from other components present in the drill cutting, such as mineral, pipe dope, or filtrate of oil base muds.

If the screen reading exceeds 999, the maximum allowable for a home screen, the sample should be diluted 1:10. This is performed by using a 1 milliliter pipette with a pipette pump to transfer from the remaining 2 ml in the syringe barrel of the injector assembly into a large test tube (16×125 mm). Then add 9 mm of IPA using a Repipet II Dispenser (5 ml+4 ml) to yield a 1:10 dilution. Once the dilution is prepared and mixed, allow the remaining 1 ml to drain out of the syringe barrel of the injector assembly and rinse it with about 3-5 ml IPA. Observe the reading on the screen decreasing towards zero. Pour about 5 ml of the 1:10 dilution sample into the syringe barrel and allow it to flow to the 2 cc mark. Press "*" on the screen to start the discrete sample averaging and record the reading once the fluorometer indicates "DONE". Multiply this reading obtained by the dilution factor.

In some cases it is also recommended to estimate the amount of iron filings in order to adjust the fluorescence intensity.

Many other variations and modifications may be made in the concepts described by those skilled in the art without departing from the concepts of the present invention. Accordingly, it should be clearly understood that the concepts disclosed in the description are illustrative only and are not intended as limitations on the scope of the invention.

What is claimed is:

1. A method for evaluating wet samples of underground formation to determine the hydrocarbon content of the formation which comprises:

solvating a known volume of a wet sample in a known volume of a polar solvent characterized by both hydrophilic and hydrophobic properties and the ability to break through a water layer of a wet cutting, solvate the commercially valuable components of the hydrocarbon and not fluoresce significantly in the wavelength range at which the fluorescence of hydrocarbons is evaluated;

mixing the solvent and wet sample;

filtering the solvent/wet sample solution; and quantitatively measuring with a fluorometer the emission fluorescence of the solvated sample below about 400 nm at an excitation wavelength at which most petroleum compounds fluoresce, and determining the hydrocarbons present in the sample by comparing the emission fluorescence of said solvated sample to the emission fluorescence of known samples, wherein correlations are drawn between the emission fluorescence of said solvated samples and the emission fluorescence of known samples.

2. The method of claim 1 wherein the polar, hydrophilic, hydrophobic solvent is selected from the group consisting of alcohols, acetates and ketones having the ability to dissolve through a water layer, solvate said commercially valuable components of the wet hydrocarbon sample, and not fluoresce significantly at an excitation wavelength at which most petroleum compounds fluoresce.

3. The method of claim 1 wherein the polar solvent is selected from the group consisting of methanol, ethanol, ethyl acetate, 1-propanol, 2-propanol(isopropanol), 2-methyl-2-propanol and allyl alcohol.

4. The method of claim 3 wherein the solvent is isopropyl alcohol.

5. The method of claim 1 wherein the wet samples are selected from the group consisting of wet rock samples, wet drill cuttings, wet core samples, and water samples.

6. The method of claim 5 wherein the wet samples are wet drill cuttings.

7. The method of claim 6 wherein the emission fluorescence is measured between about 300 and 400 nanometers.

8. The method of claim 6 wherein the sample is excited between about 245 and 310 nanometers.

9. A method of evaluating wet cuttings samples from an underground formations to determine the hydrocarbon content of the portion of the formation from which a sample came, which comprises the steps of:

solvating a known volume of wet cuttings samples in a known volume of solvent selected from the group consisting of methanol, ethanol, ethyl acetate, 1-propanol, 2-propanol, 1-propyl alcohol, 2-methyl-2-propanol, and allyl alcohol to break through the water layer and extract the commercially valuable components from the sample;

mixing said wet cuttings samples and solvent;

filtering the solution to derive an extract solution;

quantitatively measuring with a fluorometer the emission fluorescence of said extract solution between about 250 and about 400 nanometers; and determining the hydrocarbon content of any hydrocarbon present in said extract solution by comparing the emission fluorescence of said extracted solution to the emission fluorescence of known extracted solution samples, wherein correlation are drawn between the emission fluorescence of known hydrocarbon extracted solution samples in said solvent.

* * * * *